United States Patent [19]

Tomita et al.

[11] Patent Number: 5,656,591

[45] Date of Patent: Aug. 12, 1997

[54] ANTIMICROBIAL AGENTS AND METHOD FOR TREATING PRODUCTS THEREWITH

[75] Inventors: Mamoru Tomita; Seiichi Shimamura, both of Kanagawa; Kozo Kawase, Saitama; Yasuo Fukuwatari, Kanagawa; Mitsunori Takase, Saitama; Wayne Robert Bellamy, Kanagawa; Koji Yamauchi, Kanagawa; Hiroyuki Wakabayashi, Kanagawa; Yukiko Tokita, Kanagawa, all of Japan

[73] Assignee: Morinaga Milk Industry Co., Ltd., Tokyo, Japan

[21] Appl. No.: 256,771

[22] PCT Filed: Nov. 30, 1992

[86] PCT No.: PCT/JP92/01563

§ 371 Date: Nov. 29, 1994

§ 102(e) Date: Nov. 29, 1994

[87] PCT Pub. No.: WO93/14640

PCT Pub. Date: Aug. 5, 1993

[30] Foreign Application Priority Data

| Jan. 23, 1992 | [JP] | Japan | 4-032660 |
| Mar. 11, 1992 | [JP] | Japan | 4-052943 |
| Sep. 30, 1992 | [JP] | Japan | 4-262143 |
| Sep. 30, 1992 | [JP] | Japan | 4-262559 |

[51] Int. Cl.$^6$ .................................. A61K 37/16; A23L 3/34
[52] U.S. Cl. .................. 514/6; 514/8; 514/12; 514/21; 530/324; 530/395; 530/400; 530/833; 426/532; 426/657; 424/439
[58] Field of Search ............... 514/6, 8, 12, 21; 530/324, 395, 400, 833; 426/532, 657; 424/439

[56] References Cited

U.S. PATENT DOCUMENTS

| 4,980,163 | 12/1990 | Blackburn et al. | 434/94.63 |
| 5,198,419 | 3/1993 | Ando et al. | 514/8 |
| 5,214,028 | 5/1993 | Tomita et al. | 514/6 |
| 5,317,084 | 5/1994 | Tomita et al. | 530/324 |
| 5,389,611 | 2/1995 | Tomita et al. | 514/6 |

FOREIGN PATENT DOCUMENTS

| 141507 | 8/1984 | Japan . |
| 129202 | 11/1987 | Japan . |
| 191205 | 7/1990 | Japan . |
| 193708 | 8/1991 | Japan . |
| 220130 | 9/1991 | Japan . |
| 504864 | 10/1991 | Japan . |

OTHER PUBLICATIONS

Tomita et al, *J. Dairy Sci*, vol. 74, No. 12, pp. 4137–4142, 1991.

Kruzel, *Chemical Abtract*, vol. 116, p. 464, Ref. #19747j, 1991 (PCT Int. Appl. WO91,13982, 19 Sep. 1991).

Saito et al, *J. Dairy Sci*, vol. 74, No. 11, pp. 3724–3730, 1991.

*Primary Examiner*—Cecilia J. Tsang
*Assistant Examiner*—Abdel A. Mohamed
*Attorney, Agent, or Firm*—Wenderoth, Lind & Ponack

[57] ABSTRACT

There is disclosed an antimicrobial agent comprising one or more of antimicrobial peptides derived from lactoferrins, and one or more of specific compounds and/or at least an antibiotic, and a method for treating matters with said antimicrobial agent. The antimicrobial agent has a potent antimicrobial activity against wide variety of microorganisms, thus it is useful not only as a medication, but also useful for making antimicrobial treatment of matters such as foods, non-medical products, and the like with safety and great efficiency.

6 Claims, No Drawings

ANTIMICROBIAL AGENTS AND METHOD FOR TREATING PRODUCTS THEREWITH

This application is a 371 of PCT/JP92/01563, filed Nov. 30, 1992.

TECHNICAL FIELD

The present invention relates to antimicrobial agents and method for treating products therewith. More particularly, the present invention relates to new antimicrobial agents having excellent antimicrobial activity against a wide, variety of microorganisms, and method for safely treating various products, e.g., foods, medicines, and the like with such an agent.

BACKGROUND ART

It is known that lactoferrin is a natural iron-binding protein occurring in vivo, e.g. in lacrima, saliva, peripheral blood, milk and the like, and that it exhibits antimicrobial activity against various harmful microorganisms belonging to the genera of Escherichia, Candida, Closridium, and the like (Journal of Pediatrics, Vol. 94, Page 1, 1979). It is also known that lactoferrin exhibits antimicrobial activity, in a concentration of 0.5-80 mg/ml, against microorganisms belonging to the genera of Staphylococcus and Enterococcus (Nonnecke, B. J. and Smith, K. L.: Journal of Dairy Science, Vol. 67, page 606, 1984).

On the other hand, a number of inventions are known for peptides having antimicrobial activity against various microorganisms. Some examples of such peptides are: phosphono-tripeptide (Japanese Unexamined Patent Application Gazette No. 57(1982)-106689), phosphono dipeptide derivatives (Japanese Unexamined Patent Application Gazette No. 58(1983)-18594), and cyclic peptide derivatives (Japanese Unexamined Patent Application Gazette No. 58(1983)-213744) which are effective against Gram positive and Gram negative bacteria; peptides having antimicrobial and antiviral activities (Japanese Unexamined Patent. Application Gazette No. 59(1984)-51247); polypeptides effective against yeast (Japanese Unexamined Patent Application Gazette No. 60(1985)-130599); glycopeptides derivatives effective against Gram positive bacteria (Japanese Unexamined Patent Application Gazette Nos. 60(1985)-172998, 61(1986)-251699, 63(1988)-44598); oligopeptides effective against Gram positive bacteria (Japanese Unexamined Patent Application Gazette No. 62(1987)-22798); peptide antibiotics (Japanese Unexamined Patent Application Gazette Nos. 62(1987)-51697, 63(1988)-17897); antimicrobial peptides extracted from blood cells of Tachypleus tridentalus from North America (Japanese Unexamined Patent Application Gazette No. Heisei 2(1990)-53799); antimicrobial peptides isolated from hemolymph of bees (Japanese Unexamined Patent Application (via PCT root) Gazette No. Heisei 2(1990)-500084), and the like.

The inventors of this invention contemplated to isolation of useful substances, which do not have undesirable side effects (e.g. antigenicity) and which have heat-resistance as well as potent antimicrobial activity, from nature at a reasonable cost, and found the fact that hydrolysates of lactoferrin obtainable by acid or enzyme hydrolysis of mammalian lactoferrin, apo-lactoferrin, and/or metal chelated lactoferrin (hereinafter they are referred to as lactoferrins) have more potent heat-resistance and antimicrobial activity than unhydrolyzed lactoferrins, for which a patent application has been filed (Japanese Patent Application No. Heisei 3(1991)-171736).

Furthermore, the inventors of this invention previously found a number of peptides, originated from the lactoferrins, which do not have side effects (e.g. antigenicity), and which have heat-resistance as well as a potent antimicrobial activity, e.g. antimicrobial peptides having 20 amino acid residues (Japanese Patent Application No. Heisei 3(1991)-186260), antimicrobial peptides having 11 amino acid residues (Japanese Patent Application No. Heisei 3(1991)-48196), antimicrobial peptides having 6 amino acid residues (Japanese Patent Application No. Heisei 3(1991)-94492), antimicrobial peptides having 5 amino acid residues (Japanese Patent Application No. Heisei 39(1991)-94493), and antimicrobial peptides having 3-6 amino acid residues (Japanese Patent Application No. Heisei 3(1991)-94494), for which patent applications have been filed.

Heretofore, various studies have been made to potentiate the antimicrobial activity of lactoferrin, and IgA and glycopeptides are known as the auxiliary agents for potentiating such a physiological activity. There are many reports in this respect, for example, a method for the potentiation of the antimicrobial activity of lactoferrin by coexistence of lysozyme therewith (Japanese Unexamined Patent Application Gazette No. 62(1987)-249931), a method for potentiation of antimicrobial activity of lactoferrin by the coexistence of secretory IgA therewith (Stephens, S. et al.: Immunology; Vol. 41, Page 597, 1980) and so on. Furthermore, Spick et al. report that lactoferrin has an activity of inhibiting bacteria from adhering onto mucous membrane, and that this activity is potentiated by the coexistence of lysozyme or glycopeptides (Edit. by William, A. F. and Baum, J. D.: "Human Milk Banking", Nestle Nutrition Workshop Series, Vol. 5, Page 133, Pub. by Raven Press Books, Ltd.).

The efficacy of the combined use of lactoferrin and antibiotics has been also studied, and cephem antibiotics (Miyazaki, S. et al.: Chemotherapy, Vol. 39, Page 829, 1991), β-lactum antibiotics (Japanese Unexamined Patent Application Gazette No. Heisei 1-319463), and the like are known as the antibiotics which may potentiate antimicrobial activity upon the combined use with lactoferrin.

However, there have been no studies about the efficacy of the combined use of antimicrobial peptides derived from lactoferrins and specific compounds and/or antibiotics, consequently there have been no antimicrobial agents containing such substances as their effective ingredients. Furthermore, there has been no attempt to treat various matters such as foods, medicines and the like with such an agent.

DISCLOSURE OF INVENTION

The present invention is made under the aforementioned background. Therefore, it is an object of the present invention to provide antimicrobial agents which have potentiated antimicrobial activity by the combined use of lactoferrin-derived antimicrobial peptides, which are previously invented by the inventors, and specific compounds and/or antibiotics.

In order to realize the object, this invention provides antimicrobial agents which include as the effective ingredients: (A) one or more of antimicrobial peptides derived from lactoferrins; and (B) one or more compounds selected from the group consisting of metal-chelating protein, tocopherol, cyclodextrin, glycerin-fatty acid ester, alcohol, EDTA or a salt thereof, ascorbic acid or a salt thereof, citric acid or a salt thereof, polyphosphoric acid or a salt thereof, chitosan, cysteine, and cholic acid.

This invention also provides: antimicrobial agents which include, as the effective ingredients, (A) one or more of antimicrobial peptides derived from lactoferrins, and (C) an antibiotic; and antimicrobial agents which include, as the effective ingredients, (A) one or more of antimicrobial peptides derived from lactoferrins, (C) an antibiotic, and (B) one or more compounds selected from the group consisting of metal-chelating protein, lysozyme, tocopherol, cyclodextrin, glycerin-fatty acid ester, alcohol, EDTA or a salt thereof, ascorbic acid or a salt thereof, citric acid or a salt thereof, polyphosphoric acid or a salt thereof, chitosan, cysteine, and cholic acid.

Furthermore, this invention also provides a method for treating products with either one of said antimicrobial agents.

BEST MODE FOR CARRYING OUT THE INVENTION

In the present invention, the term "lactoferrins" includes: lactoferrin on the market; lactoferrin isolated from mammalian (humans, cows, sheep, goats, horses and the like) milk such as colostrum, transitional milk, matured milk, milk in later lactation, and the like or processed products thereof such as skim milk and whey by any conventional method (e.g. ion-exchange chromatography); apo-lactoferrin obtainable by de-ironization of lactoferrin with hydrochloric acid, citric acid, and the like; metal-saturated or partially metal-saturated lactoferrin obtainable by chelation of apo-lactyoferrin with a metal such as iron, copper, zinc, manganese, and the like. Lactoferrins purchased in the market or prepared in accordance with any known method can be used for preparation of the antimicrobial peptides.

In the present invention, the term "antimicrobial peptides derived from lactoferrins" includes: antimicrobial peptides obtainable by isolation from the decomposition product (hydrolysate) of lactoferrins; antimicrobial peptides having chemical structures (amino acid sequences) which are the same or homologous to those of said antimicrobial peptide obtained from said decomposition products of lactoferrins; antimicrobial peptide derivatives having chemical structures (amino acid sequences) which are the, same or homologous to those of said antimicrobial peptides obtained from said decomposition products of lactoferrins; and a mixture comprising any of the foregoing antimicrobial peptides or derivatives thereof.

These antimicrobial peptides derived from lactoferrins are obtainable by the methods disclosed in Japanese Patent Applications Nos. Heisei 3(1991)-186260, Heisei 3(1991)-48196, Heisei 3(1991)-94492, Heisei 3(1991)-94493, and Heisei 3(1991)-94494. For example, antimicrobial peptides can be obtained: by a method wherein lactoferrins are subjected to acid hydrolysis or enzymatic hydrolysis, then fractions containing antimicrobial peptides are collected from the resultant peptides mixture by suitable separation means such as liquid phase chromatography and the like; by a method wherein the amino acids sequences of the antimicrobial peptides obtained in the manner as mentioned above are determined by a known method (e.g. vapor phase sequencer), then synthesize the peptides by a known method (e.g. peptide synthesizer); or by any other known methods. These antimicrobial peptides derived from lactoferrins include: antimicrobial peptides having following amino acid sequences of Seq. ID. Nos. 2, and 27 or derivatives thereof (Japanese Patent Application No. Heisei 3(1991)-48196); antimicrobial peptides of Seq. ID. Nos. 3, 4, 5, and 6 or derivatives thereof (Japanese Patent Application No. Heisei 3(1991)-94492); antimicrobial peptides of Seq. ID. Nos. 7, 8, 9, and 31 or derivatives thereof (Japanese Patent Application No. Heisei 3(1991)-94493); antimicrobial peptides of Seq. ID. No. 10, 11, 12, 13, 14, 15, 16, 17, 18, 19, 20, and 21 or derivatives thereof (Japanese Patent Application No. Heisei 3(991)-94494); and antimicrobial peptides of Seq. ID. Nos. 22, 23, 24, 25, 26, 28, 29, and 30 or derivatives thereof (Japanese Patent Application No. Heisei 3(1991)-186260).

These antimicrobial peptides can be mixed as it is, or in a form of solution, concentrated liquid, or dried powder with one or more compounds and/or one or more antibiotics specified hereunder.

The specific compounds which can be mixed with said antimicrobial peptides derived from lactoferrins are: metal-chelating protein, tocopherol, cyclodextrin, glycerin-fatty acid ester, alcohol, EDTA or a salt thereof, ascorbic acid or a salt thereof, citric acid or a salt thereof, polyphosphoric acid or a salt thereof, chitosan, cysteine, cholic acid, and a mixture of two or more of the compounds enumerated above. The specific compounds enumerated can be purchased in the market, or alternatively can be prepared by any known methods.

The metal-chelating proteins include proteins which may produce a chelate compounds by coordination with metal ions., and some of which can be enumerated, for example, lactoferrin, transferrin, conalbumin, casein phosphopeptides originating from α-casein, β-casein, and the like.

α-cyclodextrin, β-cyclodextrin, γ-cyclodextrin, δ-cyclodextrin, and alkyl-derivatives thereof (branching cyclodextrin) can be enumerated as the examples of cyclodextrin.

The glycerin-fatty acid ester and derivertives thereof include ester made from fatty acid, and glycerin and/or polyglycerin.

The alcohol include mono-, di-, tri-, and poly-aliphatic alcohol, for example, ethanol, propyleneglycol, glycerol and the like can be enumerated.

It can be properly selected which of antimicrobial peptides and which of the specific compounds (metal-chelating protein, tocopherol, cyclodextrin, glycerin-fatty acid ester, alcohol, EDTA or a salt thereof, ascorbic acid or a salt thereof, citric acid or a salt thereof, polyphosphoric acid or a salt thereof, chitosan, cysteine, cholic acid, or a mixture of two or more compounds enumerated above) should be assorted in an agent, paying consideration to the use of the agent. A ratio for assortment of ingredients in a antimicrobial agent is properly determined, paying consideration to the kinds of ingredients selected and the use of the agent. In assortment, each of the ingredients can be mixed in a liquid or powder form, where any known diluents and/or excipients can be admixed as occasion demands.

Antibiotics which can be mixed with the antimicrobial peptides in another embodiment of this invention include penicillin, semisynthetic penicillin, cephem antibiotic, carbapenem antibiotics, monobactam antibiotics, aminoglycoside antibiotics, peptide antibiotics, tetracycline antibiotics, chloramphenicol, macrolide antibiotics, rifamycin, vancomycin, fosfomycin, chemically synthesized antimicrobial agent, antituberculosis drug, and polymyxin B. These antibiotics can be purchased in the market, or alternatively can be prepared in accordance with any known methods.

In a further embodiment of the antimicrobial agent in this invention, specific compounds can be added to the mixture of the antimicrobial peptides and one or more antibiotics, and they are metal-chelating protein, lysozyme, tocopherol, cyclodextrin, glycerin-fatty acid ester, alcohol, EDTA or a salt thereof, ascorbic acid or a salt thereof, citric acid or a salt thereof, polyphosphoric acid or a salt thereof, chitosan, cysteine, cholic acid, and a mixture of two or more compounds enumerated above. The compounds referred immediately above are completely the same to those used in the aforementioned embodiment except that lysozyme is further included. Lysozyme can be purchased in the market or can be prepared in accordance with any known method.

It can be properly selected: which of antimicrobial peptides derived from lactoferrins and which of antibiotics are to be assorted in an agent; and which of the optional mixtures of the antimicrobial peptides and the antibiotics and which of the specific compounds (metal-chelating protein, lysozyme, tocopherol, cyclodextrin, glycerin-fatty acid ester, alcohol, EDTA or a salt thereof, ascorbic acid or a salt thereof, citric acid or a salt thereof, polyphosphoric acid or a salt thereof, chitosan, cysteine, cholic acid, and a mixture of two or more of compounds selected therefrom) are to be mixed in an agent, paying consideration to the use of the agent. A ratio for assortment of ingredients in an antimicrobial agent is properly selected, paying consideration to the kinds of selected ingredients and the use of the agent. In assortment, each of the ingredients can be mixed in a form of liquid or powder, where any known diluents and/or excipients can be admixed as the occasion demands.

The antimicrobial agents in accordance with this invention exhibit potent antimicrobial activity against bacteria, yeast, and fungi, thus they can be used not only as medicines or drugs, but also as additives for any products such as foods and non-medical products which are taken into the bodies of humans or other animals, or which are applied onto or contacted with the body surface of humans or other animals, and for any other products which are generally desired to be prevented or inhibited from prolification of microorganisms therein. Moreover, the antimicrobial agents of this invention can be used for the treatment of any products or materials therefor. More particularly, the antimicrobial agents of this invention can be used in such a manner that: it is orally administered as it is to humans or other animals; it is added to, assorted to, sprayed to, adhered to, coated onto or impregnated into any products such as drugs (e.g. eye lotion, anti-mammititis drug, anti-diarrheals, epidermic agent against athlete's foot, and the like), non-medical pharmaceutical products (e.g. mouth-washing products, sweat suppressants hair tonic, and the like), cosmetics (e.g. hair liquid, creams, emulsions, and the like), dentifrices (e.g. tooth paste, tooth brushes, and the like), various feminine hygienic products, various products for babies (e.g. diaper, and the like), various geriatric products (e.g. denture cement, diaper, and the like), various detergents (e.g. toilet soaps, medicinal soaps, shampoo, rinse, laundry detergents, kitchen detergents, house detergents, and the like), various sterilized products (e.g. disinfectant-impregnated paper for kitchen, disinfectant-impregnated paper for toilet, and the like), feedstuff (e.g. feed for domestic animals and pets, and the like), materials therefor, as well as any other products which are desired to be sterilized or prevented from microbial pollution. The antimicrobial agents can be used for treatment of any matters which are generally desired to be prevented or inhibited from prolification of microorganisms.

As will be apparent from the tests described hereinafter, it is worthy of special mention that the antimicrobial agents of this invention exhibit remarkable antimicrobial activity against microorganisms, which are resistant to most of antibiotics, thus single use of the antibiotic is not effective and which causes the problem of Hospital Infection, for example, Methicilin-resistant Staphylococcus aureus.

Now, the present invention will be explained in further detail by way of some exemplifying tests.

(I) TESTS FOR ANTIMICROBIAL AGENTS CONTAINING LACTOFERRIN HYDROLYSATE AND/OR ANTIMICROBIAL PEPTIDES DERIVED FROM LACTOFERRIN, AND SPECIFIED COMPOUNDS AS THE EFFECTIVE INGREDIENTS THEREOF

Firstly, preparation of samples and methods which are commonly used in the following tests will be described.

1. Preparation of Samples (1) Lactoferrin Hydrolysate (Powder)

① Lactoferrin Hydrolysate 1 prepared in accordance with the method stated in Reference Method 1 (infra) was used.

② Lactoferrin hydrolysate 2 prepared in accordance with the method stated in Reference Method 2 (infra) was used.

(2) Antimicrobial Peptide (Powder)

① The peptide (Seq. ID Number 26) prepared in accordance with the method stated in Example 1 (infra) was used.

② The peptide (Seq. ID 27) prepared in accordance with the method stated in Example 2 (infra) was used.

(3) Lactoferrin: Bovine lactoferrin on the market (by Sigma Company) was used.

(4) Caseinphosphopeptide: Caseinphosphopeptide prepared in accordance with the known method (the method referred in Japanese Unexamined Patent Application Gazette No. 59-159792) was used.

(5) Tocopherol: A commercial product (by Wakoh Junyaku Kohgyoh Company) was used.

(6) β-Cyclodextrin: A commercial product (Nippon Shokuhin Kakoh Company) was used.

(7) 1-Monocapryloyl-rac-Glycerol: A commercial product (by Sigma Company) was used.

(8) Ethyl Alcohol: 99.5% ethyl alcohol on the market (by Nakaraitesk Company) was used.

(9) Glycerol: A commercial product (by Nakaraitesk Company) was used.

(10) Propylene Glycol: A commercial product (by Wakoh Junyaku Kohgyoh Company) was used.

(11) EDTA·$Na_2$: A commercial product (by Wakoh Junyaku Kohgyoh Company) was used.

(12) Ascorbic Acid: A commercial product (by Kantoh Kagaku Company) was used.

(13) Citric Acid: A commercial product (by Nakaraitesk Company) was used.

(14) Polyphosphoric Acid: A commercial product (by Merck Company) was used.

(15) Chitosan: A commercial product (by Nakaraitesk Company) was used. The product was dissolved in a weak solution of acetic acid.

(16) L-Cysteine: A commercial product (by Sigma Company) was used. Aqueous solution of the product was sterilized by filtaration.

(17) Polyethylene Glycol #2000: A commercial product (by Nakaraitesk Company) was used.

(18) Glycerin-Fatty Acid Ester:

① 1-monolauryl-rac-glycerol: A commercial product (by Sigma Company) was used.

② 1-monomyristoyl-rac-Glycerol: A commercial product (by Sigma Company) was used.

③ 1-monostearoyl-rac-glycerol: A commercial product (by Sigma Company) was used.

Either one was used in a form of an aqueous suspension.

(19) Cholic Acid: A commercial product (by Nakoh Junyaku Kohgyoh Company) was used in an aqueous suspension.

2. Method (1) Preparation of Preculture of Staphylococcus:

From the preservation slant of Staphylococcus aureus (JCM-2151), a loop of the bacterial strain was taken out and spread onto standard agar culture medium (by Eiken Kagaku Company) then cultivated for 16 hours at 37° C. The colonies grown on the culture medium were scraped by a platinum loop and cultivated in 1% peptone (by Difco Company) culture medium for several hours at 37° C., and the resultant microbial culture at logarithmic phase was used as the preculture in a serial concentration of $3 \times 10^8$/ml.

(2) Preparation of Basal Medium (Cow's Milk Medium):

A quantity of commercial cow's milk was diluted 2-fold with distilled water, the resultant liquid was sterilized at 115° C. for 15 minutes, to thereby obtain the basal medium.

(3) Preparation of Test and Control Media:

(3-1) Preparation of Test Media

Aqueous solutions of the samples of lactoferrin hydrolysates (sample (1), in Preparation of Samples, supra), the samples of antimicrobial peptides (sample (2), supra), and the samples of compounds (3), (4), (6), (11), (12), (13), and (16) (in Preparation of Samples, supra) were respectively dealt with sterilization filters (by Advantec Company). A quantity of the resultant solutions of the samples were selectively mixed with a quantity of the basal medium, thereby test media for the respective tests were prepared in the combinations and eventual concentrations as specified in the respective tests.

Utilizing the samples (5), (7), (8), (9), (10), (14), (15), (17), (18) and (19), test media were prepared in the same manner as in the preparation of the test media containing sample (3) and the like, except that the aqueous solution (in the cases of samples (5) and (7), aqueous suspensions) were not dealt with sterilization filters.

(3-2) Preparation of Control Medium 1

A quantity of commercial cow's milk was diluted 2-fold with distilled water, the resultant liquid was sterilized at 115° C. for 15 minutes, thereby control medium 1 was obtained.

(3-3) Preparation of Control Media 2

Aqueous solutions of the samples of the compounds (3), (4), (6), (11), (12), (13), and (16) referred in Preparation of Samples were respectively sterilized with filters (by Advantec Company), a quantity of the resultant solutions of the samples were selectively mixed with a quantity of the basal medium so that control media 2 were prepared in the combination of samples and in the concentrations corresponding to those in the test media.

Utilizing the samples of the compounds (5), (7), (8), (9), (10), (14), (15), (17), (18) and (19) (in Preparation of Samples, supra), control media 2 were prepared in the same manner as in the preparation of the control control media 1 containing samples (3) and the like, except that aqueous solutions (in the cases of the samples (5) and (7), aqueous suspensions) were not sterilized with filters.

(4) Viability Assay

To 2 ml aliquots of test media prepared in (3-1) (supra), 20 ml aliquots of the preculture of Staphylococcus aureus prepared in (1) (2. Method, supra) were added, then incubated at 37° C. for 1 hour, 200 µl aliquots of the resultant cultures were taken out and diluted with 1% peptone solution in a series of $10^n$ respectively, 110 µl aliquots of the resultant dilution series were spread onto plates of standard agar culture medium, and after incubation at 37° C. for 24 hours the number of colonies grown on the plates were counted (Test. Colony Count).

Control coloney counts 1 were determined in the same manner as in the determination of the test coloney counts, except that 20 ml aliquots of the preculture of Staphylococcus aureus prepared in (1) (2. Method, supra) were added to 2 ml aliquots of the respective control media 1 prepared in (3-2) (supra). Furthermore, control coloney counts 2 were determined in the same manner as in the determination of the test coloney counts, except that 20 ml aliquots of the preculture of Staphylococcus aureus prepared in (1) (supra) were added to 2 ml aliquots of the respective control media 1 prepared in (3-2) (supra).

Survival rates were calculated in accordance with the following formula.

Survival rate 1=(Test Colony Count/Control Colony Count 1)×100

Survival rate 2=(Control Colony Count 2/Control Colony Count 1)×100

(Note: In the tables shown hereinafter, vulues of survival rate 2 are indicated in the row where the concentration of antimicrobial peptide or lactoferrin hydrolysate is 0.)

Test 1

Viability assay was made in such a manner that the eventual concentrations of the antimicrobial peptide (Seq. ID No. 26, infra) of (2)-① in Preparation of Samples (supra) were adjusted to 0 mg, 0.5 mg, 1 mg, and 2 mg pre ml, and those of the lactoferrin of (3) were adjusted to 0 mg, 0.1 mg, 1 mg, and 10 mg per ml respectively.

The results are shown in Table 1. As will be apparent from Table 1, it is confirmed that the coexistence of lactoferrin augments the antimicrobial activity of the peptide. On the other hand, in the case wherein antimicrobial peptide was not added, but lactoferrin was added, no antimicrobial activity was observed. Therefore, it is apparent that the augmentation of antimicrobial activity is results from the potentiation due to the coexistence of the antimicrobial peptide and the lactoferrin. In addition, similar assays were made with respect to antimicrobial peptides other than that specified above and lactoferrin hydrolysates, thereby it is confirmed that antimicrobial activity was potentiated by the coexistence of lactoferrin.

TABLE 1

| concentration of lactoferrin | survival rate concentration of antimicrobial peptide (mg/ml) | | | |
|---|---|---|---|---|
| (mg/ml) | 0 | 0.5 | 1 | 2 |
| 0 | 100 | 83 | 15 | 3.5 |
| 0.1 | 150 | 60 | 7.1 | 2.2 |
| 1 | 150 | 43 | 5.0 | 1.8 |
| 10 | 104 | 8.3 | 0.3 | 0.1 |

Test 2

Viability assay was made in such a manner that the eventual concentrations in serial dilution of the antimicrobial peptide, of (2)-① in Preparation of Samples (supra) were adjusted to 0 mg, 0.5 mg, 1 mg, and 2 mg per ml, and those of the caseinphosphopeptide of (4) were adjusted to 0 mg, 1 mg, 10 mg, and 20 mg per ml respectively.

The results are shown in Table 2. As will be apparent from Table 2, it is confirmed that the presence of caseinphosphopeptide augments the antimicrobial activity of the peptide.

On the other hand, in the case wherein antimicrobial peptide was not added, but caseinphosphopeptide was added, no antimicrobial activity was observed. Therefore, it is apparent that the augmentation of antimicrobial activity results from the potentiation due to coexistence of the antimicrobial peptide and the caseinphosphopeptide. In addition, similar assays were made utilizing antimicrobial peptides other than that specified above and lactoferrin hydrolysates, thereby it is confirmed that antimicrobial activity was potentiated by the coexistence of caseinphosphopeptide.

TABLE 2

| concentration of caseinphospho-peptide (mg/ml) | survival rate concentration of antimicrobial peptide (mg/ml) | | | |
| --- | --- | --- | --- | --- |
| | 0 | 0.5 | 1 | 2 |
| 0 | 100 | 69 | 15 | 4.6 |
| 1 | 132 | 34 | 3.5 | 1.4 |
| 10 | 129 | 14 | 1.9 | 0.5 |
| 20 | 150 | 10 | 0.7 | 0.2 |

Test 3

Viability assay was made in such a manner that the eventual concentrations of the antimicrobial peptide of (2)-① in Preparation of Samples (supra) were adjusted to 0 mg, 0.5 mg, 1 mg, and 2 mg pre ml, and those of the tocopherol of (5) (supra) were adjusted to 0 mg, 0.1 mg, 0.5 mg, and 1 mg per ml respectively.

The results are shown in Table 3. As will be apparent from Table 3, it is confirmed that the presence of tocopherol augments the antimicrobial activity of the peptide. On the other hand, in the case wherein antimicrobial peptide was not added, but tocopherol was added, no antimicrobial activity was observed. Therefore, it is apparent that the augmentation of antimicrobial activity is resulted from potentiation due to coexistence of the antimicrobial peptide and the tocopherol. In addition, similar assays were made utilizing antimicrobial peptides other than that specified above and lactoferrin hydrolysates, thereby it is confirmed that antimicrobial activity was potentiated by the coexistence of the tocopherol.

TABLE 3

| concentration of tocopherol (mg/ml) | survival rate concentration of antimicrobial peptide (mg/ml) | | | |
| --- | --- | --- | --- | --- |
| | 0 | 0.5 | 1 | 2 |
| 0 | 100 | 77 | 35 | 12 |
| 0.1 | 101 | 33 | 15 | 5.2 |
| 0.5 | 113 | 14 | 6.3 | 2.4 |
| 1 | 112 | 7.9 | 3.5 | 0.9 |

Test 4

Viability assay was made in such a manner that the eventual concentrations of the antimicrobial peptide of (2)-① in Preparation of Samples (supra) were adjusted to 0 mg, 0.5 mg, 1 mg, and 2 mg pre ml, and those of the β-cyclodextrin of (6) were adjusted to 0 mg, 0.1 mg, 1 mg, and 2.5 mg per ml respectively.

The results are shown in Table 4. As will be apparent from Table 4, it is confirmed that the presence of the β-cyclodextrin augments the antimicrobial activity of the peptide. On the other hand, in the case wherein the antimicrobial peptide was not added, but the β-cycledextrin was added, no antimicrobial activity was observed. Therefore, it is apparent that the augmentation of antimicrobial activity is resulted from potentiation due to coexistence of the antimicrobial peptide and the β-cycledextrin. In addition, similar assays were made with respect to antimicrobial peptides other than that specified above and lactoferrin hydrolysates, thereby it is confirmed that antimicrobial activity was potentiated by the coexistence of the β-cycledextrin.

TABLE 4

| concentration of β-cyclodextrin (mg/ml) | survival rate concentration of antimicrobial peptide (mg/ml) | | | |
| --- | --- | --- | --- | --- |
| | 0 | 0.5 | 1 | 2 |
| 0 | 100 | 45 | 17 | 8.9 |
| 0.1 | 100 | 38 | 22 | 6.4 |
| 1 | 109 | 11 | 3.6 | 1.4 |
| 2.5 | 88 | 2.5 | 1.1 | 0.2 |

Test 5

Viability assay was made in such a manner that the eventual concentrations of the antimicrobial peptide of (2)-① in Preparation of Samples (supra) were adjusted to 0 mg, 0.5 mg, 1 mg, and 2 mg pre ml, and those of the monocapryloyl-glycerol of (7) were adjusted to 0 mg, 0.5 mg, 1 mg, and 2 mg per ml respectively.

The results are shown in Table 5. As will be apparent from Table 5, itis confirmed that the coexistence of monocapryloyl-glycerel augments the the antimicrobial activity of the peptide. On the other hand, in the case wherein said antimicrobial peptide were not added, but monocapryloyl-glycerol was added, no antimicrobial activity was observed. It is apparent that the augmentation of antimicrobial activity is resulted from potentiation due to the coexistence of the antimicrobial peptide and the monocapryloyl-glycerol, since the potentiation of the antimicrobial activity was far stronger in the case wherein the antimicrobial peptide coexisted with 2 mg/ml of the monocapryloyl-glycerol than in the cases wherein monocapryloyl-glycerol (2 mg/ml) alone or antimicrobial peptide (in all concentrations in the serial dilution) alone was included. In addition, similar assays were made utilizing antimicrobial peptides other than that specified above and lactoferrin hydrolysates, thereby it is confirmed that antimicrobial activity was potentiated by the coexistence of monocapryloyl-glycerol.

TABLE 5

| concentration of monocapryloyl-glycerol (mg/ml) | survival rate concentration of antimicrobial peptide (mg/ml) | | | |
| --- | --- | --- | --- | --- |
| | 0 | 0.5 | 1 | 2 |
| 0 | 100 | 79 | 38 | 9.5 |
| 0.5 | 103 | 81 | 40 | 7.3 |
| 1 | 115 | 18 | 6.0 | 1.5 |
| 2 | 35 | 0.1 | 0.03 | 0.01 |

Test 6

Viability assay was made in such a manner that the eventual concentrations of the antimicrobial peptide of (2)-① in Preparation of Samples (supra) were adjusted to 0 mg, 0.5 mg, 1 mg, and 2 mg pre ml, and those of the ethyl alcohol of (8) (supra) were adjusted to 0 mg, 1 mg, 10 mg, and 20 mg per ml respectively.

The results are shown in Table 6. As will be apparent from Table 6, it is confirmed that the ethyl alcohol in a low concentration potentiates the antimicrobial activity of the peptide. On the other hand, in the case wherein the antimicrobial peptide was not added, but the ethyl alcohol was added, no antimicrobial activity was observed. Therefore, it is apparent that the augmentation of antimicrobial activity is results from the potentiation due to the coexistence of the antimicrobial peptide and the ethyl alcohol. In addition, similar assays were made utilizing antimicrobial peptides other than that specified above and lactoferrin hydrolysates, thereby it is confirmed that antimicrobial activity was potentiated by the coexistence of the ethyl alcohol.

TABLE 6

| concentration of ethyl alcohol | survival rate concentration of antimicrobial peptide (mg/ml) | | | |
|---|---|---|---|---|
| (mg/ml) | 0 | 0.5 | 1 | 2 |
| 0 | 100 | 72 | 5.9 | 1.9 |
| 1 | 159 | 50 | 0.2 | 0.5 |
| 10 | 118 | 20 | 0.7 | 0.2 |
| 20 | 155 | 11 | 0.9 | 0.1 |

Test 7

Viability assay was made in such a manner that the eventual concentrations of the antimicrobial peptide of (2)-① in Preparation of Samples (supra) were adjusted to 0 mg, 0.5 mg, 1 mg, and 2 mg pre ml, and those of the glycerol of (9) were adjusted to 0 mg, 1 mg, 10 mg, and 20 mg per ml respectively.

The results are shown in Table 7. As will be apparent from Table 7, it is confirmed that the coexistence of glycerol augments the antimicrobial activity of the peptide. On the other hand, in the case wherein the antimicrobial peptide was not added, but the glycerol was added, no antimicrobial activity was observed. Therefore, it is apparent that the augmentation of antimicrobial activity results from the potentiation due to the coexistence of the antimicrobial peptide and the glycerol. In addition, similar assays were made utilizing antimicrobial peptides other than that specified above and lactoferrin hydrolysates, thereby it is confirmed that antimicrobial activity was potentiated by the coexistence of glycerol.

TABLE 7

| concentration of glycerol | survival rate concentration of antimicrobial peptide (mg/ml) | | | |
|---|---|---|---|---|
| (mg/ml) | 0 | 0.5 | 1 | 2 |
| 0 | 100 | 85 | 35 | 7.2 |
| 1 | 100 | 9.1 | 1.6 | 0.7 |
| 10 | 116 | 4.5 | 2.5 | 0.9 |
| 20 | 123 | 5.2 | 1.7 | 1.1 |

Test 8

Viability assay wag made with adjusting the eventual concentration of antimicrobial peptide of (2)-① in Preparation of Samples (supra) to 0 mg, 0.5 mg, 1 mg, and 2 mg per ml, and those of the propylene glycerol of (10) to 0 mg, 1 mg, 10 mg, and 20 mg per ml respectively.

The results are shown in Table 8. As will be apparent from Table 8, it is confirmed that propylene glycol augmented the antimicrobial activity of the peptide. On the other hand, in the case wherein the antimicrobial peptide was not added, but the propylene glycol was added, no antimicrobial activity was observed. Therefore, it is apparent that the augmentation of antimicrobial activity results from potentiation due to coexistence of the antimicrobial peptide and the propylene glycol. In addition, similar assays were made utilizing antimicrobial peptides other than that specified above and lactoferrin hydrolysates, thereby it is confirmed that antimicrobial activity was potentiated by the coexistence of propylene glycol.

TABLE 8

| concentration of propylene glycol | survival rate concentration of antimicrobial peptide (mg/ml) | | | |
|---|---|---|---|---|
| (mg/ml) | 0 | 0.5 | 1 | 2 |
| 0 | 100 | 61 | 35 | 20 |
| 1 | 82 | 23 | 5.5 | 3.2 |
| 10 | 118 | 9.8 | 7.5 | 1.5 |
| 20 | 118 | 5.6 | 5.2 | 1.8 |

Test 9

Viability assay was made in such a manner that the eventual concentrations of the lactoferrin hydrolysate 1 of (1)-① in Preparation of Samples (supra) were adjusted to 0 mg, 10 mg, 20 mg, and 40 mg per ml, and those of the EDTA. $Na_2$ of (11) were adjusted to 0 mg, 0.1 mg, 1 mg and 5 mg per ml respectively.

The results are shown in Table 9. As will be apparent from Table 9, it is confirmed that the EDTA•$Na_2$ augments the antimicrobial activity of the lactoferrin hydrolysate. On the other hand, in the case wherein the lactoferrin hydrolysate 1 was not added, but the EDTA•$Na_2$ was added, no antimicrobial activity was observed. Therefore, it is apparent that the augmentation of antimicrobial activity results from potentiation, due to coexistence of the lactoferrin hydrolysate 1 and the EDTA•$Na_2$. In addition, similar assays were made substituting lactoferrin hydrolysate 1 with antimicrobial peptides, thereby it is confirmed that antimicrobial activity was potentiated by the coexistence of EDTA•$Na_2$.

TABLE 9

| concentration of EDTA.$Na_2$ | survival rate concentration of lactoferrin hydrolysate (mg/ml) | | | |
|---|---|---|---|---|
| (mg/ml) | 0 | 10 | 20 | 40 |
| 0 | 100 | 90 | 11 | 3.7 |
| 0.1 | 122 | 48 | 5.2 | 1.8 |
| 1 | 115 | 19 | 0.4 | 0.3 |
| 5 | 101 | 4.5 | 0.2 | 0.1 |

Test 10

Viability assay was made in such a manner that the eventual concentrations of the lactoferrin hydrolysate 1 (1)-① in Preparation of Samples (supra) were adjusted to 0 mg, 10 mg, 20 mg, and 40 mg per, ml, and those of the ascorbic acid of (12) were adjusted to 0 mg, 0.1 mg, 0.5 mg and 1 mg per ml respectively.

The results are shown in Table 10. As will be apparent from Table 10, it is confirmed that ascorbic acid augments the antimicrobial activity of the lactoferrin hydrolysate 1. On the other hand, in the case wherein the lactoferrin hydrolysate 1 was not added, but the ascorbic acid was added, no antimicrobial activity was observed. Therefore, it is apparent that the augmentation of the antimicrobial activity results from potentiation due to coexistence of the lactoferrin hydrolysate 1 and the ascorbic acid. In addition, similar assays were made substituting the lactoferrin hydrolysate 1 with antimicrobial peptides, thereby it is confirmed that antimicrobial activity was potentiated by the coexistence of ascorbic acid.

TABLE 10

| concentration of ascorbic acid | survival rate concentration of lactoferrin hydrolysate (mg/ml) | | | |
|---|---|---|---|---|
| (mg/ml) | 0 | 10 | 20 | 40 |
| 0 | 100 | 85 | 12 | 5.5 |
| 0.1 | 122 | 41 | 11 | 2.6 |
| 0.5 | 115 | 15 | 2.5 | 0.8 |
| 1 | 132 | 17 | 0.8 | 0.2 |

Test 11

Viability assay was made in such a manner that the eventual concentrations of the lactoferrin hydrolysate 1 of (1)-① in Preparation of Samples (supra) were adjusted to 0 mg, 10 mg, 20 mg, and 40 mg per ml, and those of the citric acid of (13) (supra) were adjusted to 0 mg, 0.1 mg, 1 mg and 5 mg per ml respectively.

The results are shown in Table 11. As will be apparent from Table 11, it is confirmed that the citric acid augments the antimicrobial activity of the lactoferrin hydrolysate 1. On the other hand, in the case wherein the lactoferrin hydrolysate 1 was not added, but the ascorbic acid was added, no antimicrobial activity was observed. Therefore, it is apparent that the augmentation of antimicrobial activity results from potentiation due to coexistence of the lactoferrin hydrolysate 1 and the citric acid. In addition, similar assays were made substituting the lactoferrin hydrolysate 1 with antimicrobial peptides, thereby it is confirmed that the antimicrobial activity was potentiated by the coexistence of citric acid.

TABLE 11

| concentration of citric acid | survival rate concentration of lactoferrin hydrolysate (mg/ml) | | | |
|---|---|---|---|---|
| (mg/ml) | 0 | 10 | 20 | 40 |
| 0 | 100 | 75 | 6.2 | 2.0 |
| 0.1 | 148 | 41 | 2.8 | 3.4 |
| 1 | 140 | 28 | 1.9 | 1.1 |
| 5 | 130 | 16 | 0.8 | 0.5 |

Test 12

Viability assay was made in such a manner that the eventual concentrations of the lactoferrin hydrolysate 1 of (1)-① in Preparation of Samples (supra) were adjusted to 0 mg, 10 mg, 20 mg, and 40 mg per ml, and those of the polyphosphoric acid of (14) were adjusted to 0 mg, 0.1 mg, 1 mg and 5 mg per ml respectively.

The results are shown in Table 12. As will be apparent from Table 12, it is confirmed that the presence of polyphosphoric acid augments the antimicrobial activity of the lactoferrin hydrolysate 1. On the other hand, in case wherein the lactoferrin hydrolysate 1 was not added, but the polyphosphoric acid was added, no antimicrobial activity was observed. Therefore, it is apparent that the augmentation of antimicrobial activity results from potentiation due to coexistence of the lactoferrin hydrolysate 1 and the polyphosphoric acid. In addition, similar assays were made substituting the lactoferrin hydrolysate 1 with antimicrobial peptides, thereby it is confirmed that antimicrobial activity was potentiated by the coexistence of polyphosphoric acid.

TABLE 12

| concentration of polyphosphoric acid (mg/ml) | survival rate concentration of lactoferrin hydrolysate (mg/ml) | | | |
|---|---|---|---|---|
| | 0 | 10 | 20 | 40 |
| 0 | 100 | 74 | 8.2 | 2.2 |
| 0.1 | 140 | 20 | 1.1 | 0.9 |
| 1 | 124 | 15 | 0.3 | 1.3 |
| 5 | 111 | 3.5 | 0.4 | 0.3 |

Test 13

Viability assay was made in such a manner that the eventual concentrations in serial dilution of the antimicrobial peptide (Seq. ID No. 27) of (2)-② in Preparation of Samples (supra) were adjusted to 0 mg, 0.5 mg, 1 mg, and 2 mg per ml, and those of the chitosan of (15) were adjusted to 0 mg, 0.004 mg, 0.02 mg and 0.1 mg per ml respectively.

The results are shown in Table 13. As will be apparent from Table 13, it is confirmed that the presence of the ascorbic acid augments the antimicrobial activity of the peptide. On the other hand, in the case wherein the antimicrobial peptide was not added, but chitosan was added, antimicrobial activity was low. Therefore, it is apparent that the augmentation of antimicrobial activity results from potentiation due to coexistence of the antimicrobial peptide and the chitosan. In addition, similar assays were made substituting the antimicrobial peptide with lactoferrin hydrolysates, thereby it is confirmed that antimicrobial activity was potentiated by the coexistence of chitosan.

TABLE 13

| concentration of chitosan | survival rate concentration of antimicrobial peptide (mg/ml) | | | |
|---|---|---|---|---|
| (mg/ml) | 0 | 0.5 | 1 | 2 |
| 0 | 100 | 100 | 85 | 21 |
| 0.004 | 108 | 94 | 8.5 | 2.2 |
| 0.02 | 71 | 41 | 2.1 | 0.4 |
| 0.1 | 5.2 | 1.4 | 0.2 | 0.05 |

Test 14

Viability assay was made in such a manner that the eventual concentrations of the antimicrobial peptide of (2)-② in Preparation of Samples (supra) were adjusted to 0 mg, 0.5 mg, 1 mg, and 2 mg per ml, and those of the L-cysteine of (16) were adjusted to 0 mg, 1 mg, 5 mg and 10 mg per ml respectively.

The results are, shown in Table 14. As will be apparent from Table 14, it is confirmed that the presence of the L-cysteine augments the antimicrobial activity of the peptide. On the other hand, in the case wherein the antimicrobial peptide was not added, but the L-cysteine was added, antimicrobial activity was low. Therefore, it is apparent that the augmentation of antimicrobial activity results from potentiation due to coexistence of the antimicrobial peptide and the L-cysteine. In addition, similar assays were made substituting the antimicrobial peptide with lactoferrin hydrolysates, thereby it is confirmed that antimicrobial activity was potentiated by the coexistence of the L-cysteine.

TABLE 14

| concentration of L-cysteine | survival rate concentration of antimicrobial peptide (mg/ml) | | | |
|---|---|---|---|---|
| (mg/ml) | 0 | 0.5 | 1 | 2 |
| 0 | 100 | 78 | 25 | 15 |
| 1 | 37 | 12 | 2.3 | 0.7 |
| 5 | 4.5 | 2.1 | 0.09 | 0.03 |
| 10 | 0.3 | 0.06 | 0.02 | <0.004 |

Test 15

Viability assay was made in such a manner that the eventual concentrations of the lactoferrin hydrolysate 2 of (1)-② in Preparation of Samples (supra) were adjusted to 0 mg, 10 mg, 20 mg, and 40 mg per ml, and those of the polyethylene glycol #2000 of (17) were adjusted to 0 mg, 1 mg, 10 mg, and 20 mg per ml respectively.

The results are shown in Table 15. As will be apparent from Table 15, it is confirmed that the polyethylene glycol #2000 augments the antimicrobial activity of the lactoferrin hydrolysate 2. On the other hand, in the case wherein the lactoferrin hydrolysate 2 was not added, but the polyethylene glycol #2000 was added, no antimicrobial activity was observed. Therefore, it is apparent that the augmentation of antimicrobial activity results from potentiation due to coexistence of the lactoferrin hydrolysate 2 and the polyethylene glycol #2000. In addition, similar assays were made substituting the lactoferrin hydrolysate 2 with antimicrobial peptides, thereby it is confirmed that antimicrobial activity was potentiated by the coexistence of the polyethylene glycol #2000.

TABLE 15

| concentration of polyethylene glycol | survival rate concentration of lactoferrin hydrolysate (mg/ml) | | | |
|---|---|---|---|---|
| #2000 (mg/ml) | 0 | 10 | 20 | 40 |
| 0 | 100 | 42 | 26 | 11 |
| 1 | 69 | 39 | 20 | 9.4 |
| 10 | 69 | 34 | 54 | 5.5 |
| 20 | 62 | 8.1 | 2.3 | 0.4 |

Test 16

Viability assay was made in such a manner that the eventual concentrations of the lactoferrin hydrolysate 1 of (1)-① in Preparation of Samples (supra) were adjusted to 0 mg, 10 mg, 20 mg, and 40 mg per ml, and those of cholic acid of (19) (supra) were adjusted to 0 mg, 1 mg, 10 mg and 20 mg per ml respectively.

The results are shown in Table 16. As will be apparent from Table 16, it is confirmed that cholic acid augments the antimicrobial activity of the lactoferrin hydrolysate 1. On the other hand, in case wherein the lactoferrin hydrolysate 1 was not added, but cholic acid was added, no antimicrobial activity was observed. Therefore, it is apparent that the augmentation of the antimicrobial activity results from potentiation due to coexistence of the lactoferrine hydrolysate and the cholic acid. In addition, similar assays were made, substituting lactoferrin hydrolysate with antimicrobial peptides, thereby it is confirmed that antimicrobial activity was potentiated by the coexistence of cholic acid.

TABLE 16

| concentration of cholic acid | survival rate concentration of lactoferrin hydrolysate (mg/ml) | | | |
|---|---|---|---|---|
| (mg/ml) | 0 | 10 | 20 | 40 |
| 0 | 100 | 13 | 1.0 | 0.8 |
| 1 | 100 | 8.1 | 0.4 | 0.2 |
| 10 | 17 | 0.9 | 0.03 | 0.01 |
| 20 | 18 | 0.8 | 0.03 | 0.006 |

Test 17

Viability assay was made in such a manner that the eventual concentrations of the antimicrobial peptide (Seq. ID No. 26) of (2)-① (in Preparation of Samples, supra) were adjusted to 0 mg, 0.5 mg, 1 mg, and 2 mg per ml, and those of 1-monolauroyl-rac-glycerol of (18) (supra) were adjusted to 0 mg, 0.5 mg, 1 mg, and 2 mg per ml respectively.

The results are shown in Table 17. As will be apparent from Table 17, it is confirmed that 1-monolauroyl-rac-glycerol augments the antimicrobial activity of the antimicrobial peptide. On the other hand, in case wherein the antimicrobial peptide was not added, but 1-monolauroyl-rac-glycerol was added, almost no antimicrobial activity was observed. Therefore, it is apparent that the augmentation of antimicrobial activity results from potentiation due to coexistence of the antimicrobial peptide and the 1-monolauroyl-rac-glycerol. In addition, similar assays were made, substituting antimicrobial peptide was substituted with lactoferrin hydrolysate, thereby it is confirmed that antimicrobial activity was potentiated by the coexistence of 1-monolauroyl-rac-glycerol.

TABLE 17

| concentration of 1-monolauroyl-rac- | survival rate concentration of lactoferrin hydrolysate (mg/ml) | | | |
|---|---|---|---|---|
| glycerol (mg/ml) | 0 | 0.5 | 1 | 2 |
| 0 | 100 | 102 | 92 | 41 |
| 0.5 | 104 | 94 | 77 | 25 |
| 1 | 88 | 73 | 46 | 12 |
| 2 | 50 | 20 | 2.3 | 0.8 |

Test 18

Viability assay was made with adjusting the eventual concentrations of antimicrobial peptide of (2)-① (in Preparation of Samples, supra) to 0 mg, 0.5 mg, 1 mg, and 2 mg per ml, and those of 1-monomyristoyl-rac-glycerol of (18) (supra) to 0 mg, 0.5 mg, 1 mg and 2 mg per ml respectively.

The results are shown in Table 18. As will be apparent from Table 18, it is confirmed that the presence of the 1-monomyristoyl-rac-glycerol augmented the antimicrobial activity of the peptide. On the other hand, in the case wherein the antimicrobial peptide was not added, but 1-monomyristoyl-rac-glycerol was added, the antimicrobial activity is low. Therefore, it is apparent that the augmentation of antimicrobial activity results from potentiation due to coexistence of the antimicrobial peptide and the 1-monomyristoyl-rac-glycerol. In addition, similar assays were made, substituting the antimicrobial peptides with lactoferrin hydrolysate, thereby it is confirmed that antimicrobial activity was potentiated by the coexistence of 1-monomyristoyl-rac-glycerol.

TABLE 18

| concentration of 1-monomyristoyl-rac-glycerol (mg/ml) | survival rate concentration of antimicrobial peptide (mg/ml) | | | |
|---|---|---|---|---|
| | 0 | 0.5 | 1 | 2 |
| 0 | 100 | 85 | 56 | 23 |
| 0.5 | 129 | 41 | 11 | 5.3 |
| 1 | 93 | 13 | 3.1 | 1.2 |
| 2 | 7 | 0.3 | 0.04 | 0.005 |

Test 19

Viability assay was made in such a manner that the eventual concentrations in serial dilution of the antimicrobial peptide of (2)-① (in Preparation of Samples) were adjusted to 0 mg, 0.5 mg, 1 mg, and 2 mg per ml, and those of the 1-monostearoyl-rac-glycerol of (18) (supra) were adjusted to 0 mg, 0.5 mg, 1 mg and 2 mg per ml respectively.

The results are shown in Table 19. As will be apparent from Table 19, it is confirmed that the 1-monostearoyl-rac-glycerol augments the antimicrobial activity of the antimicrobial peptide. On the other hand, in the case wherein the antimicrobial peptide was not added, but 1-monostearoyl-rac-glycerol was added, no antimicrobial activity was observed. Therefore, it is apparent that the augmentation of antimicrobial activity results from potentiation due to the coexistence of the antimicrobial peptide and the 1-monostearoyl-rac-glycerol. In addition, similar assays were made, substituting antimicrobial peptide with lactoferrin hydrolysate; thereby it is confirmed that the antimicrobial activity was potentiated by the coexistence of 1-monostearoyl-rac-glycerol.

TABLE 19

| concentration of 1-monostearoyl-rac-glycerol (mg/ml) | survival rate (%) concentration of antimicrobial peptide (mg/ml) | | | |
|---|---|---|---|---|
| | 0 | 0.5 | 1 | 2 |
| 0 | 100 | 69 | 43 | 21 |
| 0.5 | 116 | 74 | 53 | 18 |
| 1 | 133 | 48 | 19 | 5.5 |
| 2 | 98 | 25 | 5.3 | 1.7 |

Test 20

Viability assay was made in such a manner that the eventual concentrations of the antimicrobial peptide of (2)-② (in Preparation of Samples, supra) were adjusted to 0 mg and 1 mg per ml, those of 1-monolauroyl-rac-glycerol of (18) (supra) were adjusted to 0 mg and 0.5 mg per ml, those of the bovine lactoferrin of (3) (supra) were adjusted to 0 mg, and 1 mg per ml respectively.

The results are shown in Table 20. As will be apparent from Table 20, it is confirmed that the presence of 1-monolauroyl-rac-glycerol and bovine lactoferrin further augments the antimicrobial activity of the antimicrobial peptides. Furthermore, additional tests were made, substituted the antimicrobial peptide specified above with lactoferrin hydrolysate, thereby it is confirmed that antimicrobial activity was potentiated.

TABLE 20

| antimicrobial peptide (mg/ml) | 1-monolauroyl rac-glycerol (mg/ml) | bovine lactoferrin (mg/ml) | survival rate (%) |
|---|---|---|---|
| 0 | 0 | 0 | 100 |
| 1 | 0 | 0 | 76 |
| 0 | 0.5 | 0 | 87 |
| 0 | 0 | 1 | 105 |
| 1 | 0.5 | 0 | 2.1 |
| 1 | 0 | 1 | 63 |
| 0 | 0.5 | 1 | 66 |
| 1 | 0.5 | 1 | 0.06 |

Test 21

Viability assay was made in such a manner that the eventual concentrations of the antimicrobial peptide of (2)-② (in Preparation of Samples, supra) were adjusted to 0 mg and 1 mg per ml, and those of 1-monolauroyl-rac-glycerol of (18) (supra) were adjusted to 0 mg and 0.5 mg, and those of chitosan of (15) (supra) were adjusted to 0 mg and 0.01 mg per ml respectively.

The results are shown in Table 21. As will be apparent from Table 21, it is confirmed that the coexistence of 1-monolauroyl-rac-glycerol and chitosan further augments the antimicrobial activity of the peptide. On the other hand, similar assays were made, substituting the antimicrobial peptide with lactoferrin hydrolysate, thereby it is confirmed that antimicrobial activity was potentiated.

TABLE 21

| antimicrobial peptide (mg/ml) | 1-monolauroyl rac-glycerol (mg/ml) | chitosan (mg/ml) | survival rate (%) |
|---|---|---|---|
| 0 | 0 | 0 | 100 |
| 1 | 0 | 0 | 97 |
| 0 | 0.5 | 0 | 86 |
| 0 | 0 | 0.01 | 73 |
| 1 | 0.5 | 0 | 4.6 |
| 1 | 0 | 0.01 | 1.4 |
| 0 | 0.5 | 0.01 | 41 |
| 1 | 0.5 | 0.01 | 0.02 |

Test 22

Viability assay was made in such a manner that the eventual concentrations of the antimicrobial peptide of (2)-① (in Preparation of Samples, supra) were adjusted to 0 mg and 1 mg per ml, those of the 1-monolauroyl-rac-glycerol of (18) (supra) were adjusted to 0 mg and 0.5 mg per ml, and those of the cholic acid of (19) were adjusted to 0 mg and 1 mg per ml respectively.

The results are shown in Table 22. As will be apparent from Table 22, it is confirmed that the coexistence of the 1-monolauroyl-rac-glycerol and the cholic acid further augments the antimicrobial activity of the peptide. Moreover, similar assays were made, substituting the antimicrobial peptide with lactoferrin hydrolysate, thereby it is confirmed that antimicrobial activity was potentiated.

TABLE 22

| antimicrobial peptide (mg/ml) | 1-monolauroyl rac-glycerol (mg/ml) | cholic acid (mg/ml) | survival rate (%) |
|---|---|---|---|
| 0 | 0 | 0 | 100 |
| 1 | 0 | 0 | 72 |
| 0 | 0.5 | 0 | 58 |

TABLE 22-continued

| antimicrobial peptide (mg/ml) | 1-monolauroyl rac-glycerol (mg/ml) | cholic acid (mg/ml) | survival rate (%) |
|---|---|---|---|
| 0 | 0 | 1 | 92 |
| 1 | 0.5 | 0 | 0.2 |
| 1 | 0 | 1 | 30 |
| 0 | 0.5 | 1 | 0.6 |
| 1 | 0.5 | 1 | 0.03 |

(II) TEST FOR ANTIMICROBIAL AGENTS CONTAINING LACTOFERRIN HYDROLYSATES AND/OR ANTIMICROBIAL PEPTIDES DERIVED FROM LACTOFERRINS, AND ANTIBIOTICS OR ALTERNATIVELY ANTIBIOTICS AND SPECIFIC COMPOUNDS AS THE EFFECTIVE INGREDIENTS

Firstly, preparation of samples and methods which are commonly used in the tests described hereunder will be described.

1. Preparation of Samples (1) Lactoferrin hydrolysates (Powder)

The product prepared in accordance with the method stated in Reference Method 1 was used.

(2) Antimicrobial Peptide (Powder)

The product prepared in accordance with the method stated in Example 2 was used.

(3) Antibiotics

The antibiotics (commercial products) listed in Tables 23 and 27 were used.

(4) Lactoferrin

A commercial product of bovine lactoferrin (by Sigma Company) was used.

(5) Lysozyme

A commercial product of egg white lysozyme (by Seikagaku Kohgyoh Company) was used.

(6) 1-monocaproyl-rac-glycerol

A commercial product of 1-monocaproyl-rac-glycerol (by Sigma Company) was used.

2. Method (1) Preparation of Precultures of Test Microorganisms

Precultures of test microorganisms to be used in the tests described hereunder were prepared in such a manner that: from the frozen preservation of dispersions of test microorganisms, a loop of the respective strains of the microorganisms were taken out and spread onto TRI PETIT CASE SOYA AGAR MEDIA (by BBL Company), and incubated at 37° C. for 16 hours; the colonies grown on the culture media were scraped by a platinum loop and cultivated in 2.1% Mueller-Hington Broth (by Difco Company) respectively for several hours at 37° C. The resultant microbial cultures at logarithmic phase in $3 \times 10^8$/ml of microbial concentration were used as the precultures.

(2) Preparation of Test Media

The test media to be used in the respective tests were prepared in such a manner that: aqueous solutions in a predetermined concentration of the lactoferrin hydrolysates or the lactoferrin-derived antimicrobial peptides of (1) and (2) in Preparation of Samples (supra), as well as the samples of antibiotics of (3) (supra) were respectively sterilized with filters (by Advantec Company); then a quantity of the resultant solutions of respective samples were selectively added to a quantity of basal medium (Mueller-Hington Broth) prepared in the eventual concentration of 2.1%, thereby combinations of the samples and their concentrations in the respective test media were adjusted as specified in the respective tests.

(3) Test for Antimicrobial Activity

Antimicrobial activity was examined as follows: A quantity of the respective precultures prepared in (1) immediately above was diluted with 2.1% Mueller-Hington Broth to result in $2 \times 10^6$/ml of microbial concentration; 100 µl aliquots of the resultant liquid were added to 100 µl aliquots of one of the test media as specified in the respective test; the resultant media were incubated at 37° C. for 16 hours; then the turbidity of the resultant culture broths were measured thereby antimicrobial activity was examined.

(4) Viability Assay

Survival rate was examined in such a manner that: 20 µl aliquots of the respective precultures prepared in (1) immediately above were added to 2 ml aliquots of the respective test media prepared in paragraph (2) immediately above; the resultant media were incubated at 37° C. for an hour; 200 µl aliquots of the respective resultant culture broths were serially diluted in $10°$ with a 1% aqueous solution of peptone; 110 µl aliquots of the resultant diluted solutions were spread onto broth agar plates; after incubation at 37° C. for 24 hours the number of colonys (test colony count) grown on the plates were counted. On the other hand control colony count was enumerated in the same manner as in the enumeration of test colony count except that 20 µl aliquots of the respective precultures were added to 21 aliquots of 2.1% Mueller-Hington broth; then survival rate was calculated in accordance with following formula:

Survival Rate=(test colony count/control colony count)× 100

Test 23

Components in the test and control media and eventual concentrations thereof were adjusted by properly combining 0 mg, 0.4 mg, 1.6 mg and 6.4 mg/ml of lactoferrin hydrolysate of (1) (in Preparation of Samples, supra), or 0 µg, 16 µg, 64 µg, and 256 µg/ml of lactoferrin-derived antimicrobial peptides of (2) (in Preparation of Samples, supra), and 0 µg, 0.01 µg, 0.1 µg, 1 µg, and 10 µg/ml of antibiotics of (3) (supra), then antimicrobial activity of the combined use of the components against *Escherichia coli* 0-111 and *Staphylococcus aureus* (JCM2151) as well as growth inhibiting concentrations of the antibiotics were investigated.

The results are shown in Tables 23–26. As will be apparent from the tables, it was confirmed that the lactoferrin hydrolysates as well as the antimicrobial peptides potentiated the antimicrobial activity of the antibiotics. On the other hand, no antimicrobial activity was observed when no antibiotics were included, but either one of the lactoferrin hydrolysates or the antimicrobial peptides was included. Therefore, it is apparent that the augmentation of antimicrobial activity was resulted from potentiation due to coexistence of lactoferrin hydrolysates or antimicrobial peptides.

In addition, similar assay was made, utilizing antimicrobial peptides other than that used in this test, it Is confirmed that the antimicrobial activity of the antibiotics was potentiated by the coexistence thereof.

TABLE 23

Test Microorganism: *Escherichia coli* O-111

| antibiotics | Growth inhibiting Concentration of antibiotics (μg/ml) concentrations of lactoferrin hydrolysate (mg/ml) | | | |
|---|---|---|---|---|
| | 0 | 0.4 | 1.6 | 6.4 |
| penicillin | >1 | 1 | 1 | 0.1 |
| ampicillin | >1 | 1 | 1 | 0.01 |
| cephalothin | >1 | >1 | 1 | 0.01 |
| erythromycin | >1 | 1 | 1 | 0.1 |
| kanamycin | >1 | >1 | 1 | 0.1 |
| staphcillin | >1 | >1 | >1 | 0.1 |
| streptomycin | >1 | >1 | 1 | 0.01 |
| hostacyclin | 1 | 1 | 1 | 0.1 |
| gentamicin | 1 | 1 | 0.1 | 0.1 |
| polymyxin B | >1 | >1 | 0.1 | 0.01 |
| chloramphenicol | >1 | >1 | >1 | 0.1 |

TABLE 24

Test Microorganism: *Staphylococcus aureus* JCM2151

| antibiotics | Growth inhibiting Concentration of antibiotics (μg/ml) concentrations of lactoferrin hydrolysate (mg/ml) | | | |
|---|---|---|---|---|
| | 0 | 0.4 | 1.6 | 6.4 |
| penicillin | >1 | 1 | 1 | 0.1 |
| ampicillin | >1 | 1 | 1 | 0.1 |
| cephalothin | >1 | 1 | 1 | 0.01 |
| erythromycin | >1 | 1 | 1 | 0.01 |
| kanamycin | >1 | >1 | >1 | 0.1 |
| staphcillin | >1 | >1 | >1 | 0.1 |
| streptomycin | >1 | >1 | 1 | 0.1 |
| hostacyclin | 1 | 1 | 1 | 0.1 |
| gentamicin | 1 | 0.1 | 0.1 | 0.1 |
| polymyxin B | >1 | 0.1 | 0.1 | 0.1 |
| chloramphenicol | >1 | >1 | >1 | 1 |

TABLE 25

Test Microorganism: *Escherichia coli* O-111

| antibiotics | Growth inhibiting Concentration of antibiotics (μg/ml) concentrations of antimicrobial peptide (μg/ml) | | | |
|---|---|---|---|---|
| | 0 | 16 | 64 | 256 |
| penicillin | >1 | >1 | 1 | 0.1 |
| ampicillin | >1 | 1 | 1 | 0.1 |
| cephalothin | >1 | >1 | 1 | 0.01 |
| erythromycin | >1 | 1 | 1 | 0.01 |
| kanamycin | >1 | >1 | 1 | 0.01 |
| staphcillin | >1 | >1 | 1 | 0.01 |
| streptomycin | >1 | >1 | 1 | 0.01 |
| hostacyclin | 1 | 1 | 1 | 0.1 |
| gentamicin | 1 | 1 | 0.1 | 0.1 |
| polymyxin B | >1 | >1 | 0.1 | 0.1 |
| chloramphenicol | >1 | >1 | 1 | 0.1 |

TABLE 26

Test Microorganism: *Staphylococcus aureus* JCM2151

| antibiotics | Growth inhibiting Concentration of antibiotics (μg/ml) concentrations of antimicrobial peptides (μg/ml) | | | |
|---|---|---|---|---|
| | 0 | 16 | 64 | 256 |
| penicillin | >1 | 1 | 1 | 0.1 |
| ampicillin | >1 | 1 | 1 | 0.1 |
| cephalothin | >1 | 1 | 1 | 0.01 |
| erythromycin | >1 | 1 | 1 | 0.01 |
| kanamycin | >1 | >1 | 1 | 0.01 |
| staphcillin | >1 | >1 | 1 | 0.01 |
| streptomycin | >1 | >1 | 1 | 0.01 |
| hostacyclin | 1 | 1 | 1 | 0.1 |
| gentamicin | 1 | 0.1 | 0.1 | 0.1 |
| polymyxin B | >1 | 0.1 | 0.1 | 0.1 |
| chloramphenicol | >1 | >1 | 1 | 1 |

Test 24

Components in the test and control media and eventual concentrations thereof were adjusted by properly combining 0 μg, 10 μg, 100 μg and 1000 μg/ml of lactoferrin-derived antimicrobial peptides of (2) (in Preparation of Samples, supra), and 0 μg, 10 μg, and 50 μg/ml of antibiotics of (3) (supra), then viability assay was made on an antibiotics-resistant microorganisms (methicillin-resistant *Staphylococcus aureus* (wild type)).

The results are shown in Tables 27. As will be apparent from Table 27, it was confirmed that the antimicrobial peptides potentiated the antimicrobial activity of the antibiotics. On the other hand, no antimicrobial activity was observed when antibiotics were not included, but antimicrobial peptides were added. Therefore, it is apparent that the augmentation of the antimicrobial activity was results from potentiation due to coexistence of the antimicrobial peptides.

In addition, similar assay was made, utilizing antimicrobial peptides other than that used in this test, it is confirmed that the antimicrobial activity of the antibiotics was potentiated by the coexistence thereof.

TABLE 27

| concentration of minomycin (μg/ml) | survival rate (%) concentrations of antimicrobial peptide (μg/ml) | | | |
|---|---|---|---|---|
| | 0 | 10 | 100 | 1000 |
| 0 | 100 | 69 | 60 | 3.6 |
| 10 | 32 | 21 | 21 | 0.01 |
| 50 | 5.2 | 4.8 | 2.4 | <0.002 |

Test 25

Components in the test and control media and eventual concentrations thereof were adjusted by properly combining 0 μg and 10 μg/ml of lactoferrin-derived antimicrobial peptides of (2) (in Preparation of Samples, supra), and 10 μg and, 100 μg/ml of lactoferrin of (4) (in Preparation of Samples, supra), lysozyme of (5) (supra) or 1-monocapryloyl-rac-glycerol of (6) (supra), and 0 μg and 1 μg/ml of antibiotics of (3) (supra), then viability assay was made on *Staphylocoecus aureus* (JCM-2151).

The results are shown in Tables 28. As will be apparent from the table, the coexistence of the antimicrobial peptide, and either one of lactoferrin, lysozyme, and 1-monocapryloyl-rac-glycerol augments the antimicrobial activity of the antibiotics. On the other hand, when the antimicrobial peptide, and either one of the lactoferrin, lysozyme, and 1-monocapryloyl-rac-glycerol were added, but antibiotics was not added, almost no antimicrobial activity was observed. Therefore, it is apparent that the augmentation of the antimicrobial activity results from potentiation due to coexistence of the antimicrobial peptide, and either one of lactoferrin, lysozyme, and 1-monocapryloyl-rac-glycerol as well as the antibiotics.

In addition, similar assay was made utilizing antimicrobial peptides other than that used in this test, or lactoferrin hydrolysates, metal-chelating proteins, tocopherol, cyclodextrin, glycerine-fatty acid ester, alcohol, EDTA or a salt thereof, ascorbic acid or a salt thereof, citric acid or a salt thereof, polyphosphoric acid or a salt thereof, chitosan, cystein, or cholic acid and an antibiotics other than that used in this test, it is confirmed that the antimicrobial activity of the antibiotics was potentiated.

TABLE 28

| | survival rate (%) | | |
|---|---|---|---|
| | control | penicillin (1 µg/ml) | streptomycin (1 µg/ml) |
| control | 100 | 14.2 | 12.4 |
| antimicrobial peptide (10 µg/ml) | 60 | 0.4 | 0.2 |
| antimicrobial peptide (10 µg/ml) + lactoferrin (100 µ/ml) | 7.4 | <0.01 | <0.01 |
| antimicrobial peptide (10 µg/ml) + lysozyme (100 µ/ml) | 6.5 | <0.01 | <0.01 |
| antimicrobial peptide (10 µg/ml) + 1-monocapryloyl-rac-glycerol (100 µg/ml) | 7.3 | <0.01 | <0.01 |

As explained in detail in the foregoing tests, it will be understood that the present invention provides antimicrobial agents which have excellent antimicrobial activity against a wide variety of microorganisms, and which can be safely used for foods, drugs and the like. Since the antimicrobial agents of this invention exhibit potentiated antimicrobial activity with a minor quantity, almost no affect on the palatability of the foods when they are used for treatment thereof.

Moreover, when an antibiotic is included as one of the effective components of the antimicrobial agent, the antimicrobial activity of the antibiotic is remarkably potentiated, thus it is possible to reduce the quantity of the antibiotic to be included therein. In addition, the antimicrobial agents of this invention exhibit remarkable antimicrobial activity against microorganisms which have tolerance to a certain kinds of antibiotics.

Reference Method 1

About 1000 g of a solution of lactoferrin hydrolysate was yielded in such a manner that: 50 g of commercial lactoferrin just as isolated from cow's milk was dissolved into 950 g of distilled water; the resultant solution was heated at 120° C. for 15 minutes; after the pH of the resultant solution was adjusted to 2 with 1N hydrochloric acid; then the resultant solution of lactoferrin hydrolysate was cooled (concentration of the lactoferrin hydrolysate: 5%). The hydrolyzing rate of the product was 9%.

From the solution of lactoferrin hydrolysate, about 49 g of powdery lactoferrin hydrolysate was yielded by concentrating the solution under diminished pressure, followed by freezedrying.

Reference Method 2

About 10 kg of a solution of lactoferrin hydrolysate (concentration of the products: 10%) was yielded in such a manner that 1 kg of commercial lactoferrin (by Oreofina company, Belgium) just as isolated from cow's milk was dissolved into 9 kg of distilled water, followed by adjustment of pH to 2.5 by addition of 2 mole citric acid, addition of 30 g of commercial swine pepsin (1:10000; by Wakoh Junyaku Company) to the resultant liquid, incubation of the resultant liquid at 37° C. for 180 minutes, deactivation of the pepsin by heating at 80° C. for 10 minutes, and cooling the resultant solution. The hydrolyzing rate of the product was 11.3%.

From the solution of lactoferrin hydrolysate, about 960 g of powdery lactoferrin hydrolysate was yielded by concentrating the solution under diminished pressure, followed by freezedrying.

Now, some examples will be described hereunder more concretely and more precisely for explanation of the present invention, however, it should be noted that the present invention is not limited thereto.

EXAMPLE 1

Hydrolysis of lactoferrin was made in such a manner that: 50 mg of commercial bovine lactoferrin (by Sigma Company) was dissolved into 0.9 ml of distilled water; pH of the resultant solution was adjusted to 2.5 by addition of 0.1N hydrochloric acid; after adding 1 mg of commercial swine pepsin (by Sigma Company) the resultant solution was hydrolyzed at 37° C. for 6 hours; the pH of the resultant solution was adjusted to 7.0 with 0.1N sodium hydrooxide; then the enzyme was deactivated by heating at 80° C. for 10 minutes; the resultant liquid was cooled and centrifuged at 15,000 rpm for 30 minutes thereby a clear supernatant containing lactoferrin hydrolyzate was obtained.

One hundred (100) µl of the supernatant was passed through a column of TSK gel ODS-120T (by TOHSOH Company) at a flow rate of 0.5 ml/min., then the column was rinsed with 20% acetonitrile containing 0.05% of TFA (trifluoro acetate) for 10 minutes. Acetonitrile gradient (20–60%) containing 0.05% of TFA was further passed through the column for 30 minutes during which period a fraction eluted between 24–25 minutes was collected and dried under diminished pressure.

The resultant powder (lactoferrin hydrolysate) was dissolved into distilled water to make a 2% (w/v) solution which was passed through a column of TSK gel ODS-120T (by TOHSDH Company) at a flow rate of 0.5 ml/min. Acetonitrile (24%) containing 0–05% TFA was passed through the column for 10 minutes, then 24–32% acetonitrile gradient containing 0.05% of TFA was passed through the column for 30 minutes during which a fraction eluted between 33.5–35.5 minutes was collected. The latter HPLC procedure was repeated 25 times, the resultant eluate was dried under diminished pressure to thereby obtain 1.5 mg of antimicrobial peptide.

The resultant antimicrobial peptide was hydrolyzed with 6N hydrochloric acid, then amino acid composition thereof was analyzed with an amino acid analizer in accordance with the conventional method. The same sample was subjected to vapor phase sequencer (by Applied Bio=Systems Company) to make Edman decomposition 25 times thereby the sequence of 25 amino acid residues was determined. Also, presence of disulfide linkage in the peptide was confirmed by the disulfide-linkage analysis (Analytical Biochemistry; Vol. 67, page 493, 1975) utilizing DTNB (5,5-dithio-bis(2-nitrobenzoic acid)).

As a result, it is confirmed that this peptide have an amino acid sequence as shown in Seq ID No. 26 (infra), consisting of 25 amino acid residues, and having a disulfide linkage between 3rd and 20th cystein residues, and that two amino acid residues bonded to the 3rd cystein residue on the N-terminus side, and 5 amino acid residues bonded to the 20th cystein residue on the C-terminus side.

An antimicrobial preparation of this invention was prepared homogeneously mixing 1 g of commercial lactoferrin (by Sigma Company) to 100 mg of the powdery antimicrobial peptide.

EXAMPLE 2

An antimicrobial peptide of which amino acid sequence is known (Seq. ID No. 27) was synthesized with peptide-auto-synthesizer (LKB Bioynx 4170, by Pharmacia LKB Biotechnology Company) in accordance with Solid Phase Peptide Synthesis by Shepperd et al. (Journal of Chemical Society Perkin I., page 583, 1981), the particulars of which are as follows:

Anhydrides of desired amino acids were produced by adding N,N-dicyclohexylcarbodiimide to said amino acids of which amine-functional groups were previously protected with 9-fluorenyl methoxi carbonyl groups. The resultant Fmoc-amino acid anhydrides were used for synthesis of the peptide. Peptide chains in a known amino acid sequence were formed in such a manner that Fmoc-lysine anhydrides which correspond to the lysine residue at the C-terminus of the peptide was fixed to Ultrosyn A resin (by Pharmacia LKB Biotechnology Company) with their carboxyl groups under the presence of dimethylaminopyridine as a catalyst. Washing the resin with dimethylformamide containing pyperidine to thereby remove the protective groups bonded to amine-functional groups of the C-terminus amino acids (lysine); the Fmoc-lysine anhydrides which corrspond to 2nd amino acid from the C-terminus in the amino acid sequence were coupled to the deprotected amine-functional groups of the C-terminal lysine which was previously fixed to the resin. In the same manner, methionine, arginine, tryptophan, glutamine, tryptophan, arginine, arginine, threonine, and lysine were successively coupled to the amino acid which was coupled immediately before. When the successive coupling of all amino acids was completed, and the aimed peptide chains having the desired sequence were formed, removal of the protective groups other than acetamide-methyl and detachement of the synthesized peptides from the resin were performed by addition of a solvent consisting of 94% TFA, 5% of phenol, and 1% of ethandiol, the resultant solution of the peptide was purified with HPLC, then the purified solution was concentrated and dried to thereby obtain the peptide powder.

The amino acid composition of the resultant peptide was analyzed with an amino acid analyzer in accordance with the conventional method, thereby it is confirmed that the synthesized peptides have the amino acid sequence as shown in Seq. ID No. 27.

An antimicrobial agent of this invention was prepared by homogeneously mixing 100 mg of the synthesized antimicrobial peptide with 2 g of caseinphosphopeptide (the same one used in Test 2, supra).

EXAMPLE 3

An antimicrobial agent of this invention was prepared by homogeneously mixing 100 mg of the antimicrobial peptide prepared in the same method as in Example 1 and 1 mg of minocycline (tetracycrin antibiotics).

EXAMPLE 4

An antimicrobial agent of this invention was prepared by homogeneously mixing 100 mg of the antimicrobial peptide prepared in the same method as in Example 1 and 1 mg of penicillin G.

EXAMPLE 5

An antimicrobial agent of this invention was prepared by homogeneously mixing 10 mg of the antimicrobial peptide prepared in the same method as in Example 1, 100 mg of lysozyme, and 1 mg of penicillin G.

EXAMPLE 6

An antimicrobial agent of this invention was prepared by homogeneously mixing 100 mg of the antimicrobial peptide prepared in the same method as in Example 2 and 0.5 mg of gentamicin.

EXAMPLE 7

Eye lotion (aqueous solution) was prepared with the following ingredients in accordance with the conventional method.

| | |
|---|---|
| boric acid | 1.60 (%) |
| antimicrobial agent of Example 2 | 0.15 |
| methyl cellulose | 0.50 |

EXAMPLE 8

Skin cleanser (rinse) was prepared with the following ingredients in accordance with the conventional method. In use, the skin cleanser is diluted 50-fold with water.

| | |
|---|---|
| sodium chloride | 8.0 (%) |
| antimicrobial agent of Example 1 | 0.8 |
| distilled water | 91.2 |

EXAMPLE 9

A composition affecting epidermis (ointment) was prepared with the following ingredients in accordance with the conventional method.

| | |
|---|---|
| ethyl p-hydroxybenzoate | 0.10 (%) |
| butyl p-hydroxybenzoate | 0.10 |
| lauromacrogol | 0.50 |
| cetanol | 18.00 |
| white petrolatum | 40.00 |
| distilled water | 40.85 |
| peptide of Sequence No. 27 | 0.15 |
| 1-monomyristoyl-rac-glycerol | 0.30 |

EXAMPLE 10

Hand lotion was prepared with the following ingredients in accordance with the conventional method.

| | |
|---|---|
| carbowax 1500 | 8.00 (%) |
| alcohol | 5.00 |
| propylene glycol | 52.00 |
| distilled water | 33.90 |

-continued

| | |
|---|---|
| perfumery | 0.30 |
| peptide of Sequence No. 26 | 0.20 |
| 1-monolauroyl-rac-glycerol | 0.20 |
| cholic acid | 0.40 |

EXAMPLE 11

A composition affecting epidermis was prepared with the following ingredients in accordance with the conventional method.

| | |
|---|---|
| ethyl p-hydroxybenzoate | 0.1 (%) |
| butyl p-hydroxybenzoate | 0.1 |
| lauromacrogol | 0.5 |
| cetanol | 20.0 |
| white petrolatum | 40.0 |
| water | 29.3 |
| antimicrobial agent of Example 3 | 10.0 |

EXAMPLE 12

A therapeutic composition for mammititis was prepared with the following ingredients in accordance with the conventional method.

| | |
|---|---|
| 1,2-hydroxystearin | 0.1 (%) |
| glyceromonostearate | 0.5 |
| butylated hydroxyanisol | 0.02 |
| peanut oil | 93.48 |
| antimicrobial agent of Example 4 | 5.0 |

EXAMPLE 13

A composition affecting epidermis was prepared with the following ingredients in accordance with the conventional method.

| | |
|---|---|
| ethyl p-hydroxybenzioate | 0.1 (%) |
| butyl p-hydroxybenzoate | 0.1 (%) |
| lauromacrogol | 0.5 |
| cetanol | 20.0 |
| white petrolatum | 40.0 |
| water | 29.3 |
| antimicrobial agent of Example 5 | 10.0 |

EXAMPLE 14

Antibiotic agent having following composition was prepared in accordance with the conventional method.

| | |
|---|---|
| Antimicrobial agent of Example 6 | 100.0 (%) |

INDUSTRIAL APPLICATION

The antimicrobial agent of this invention is useful as drugs having potent antimicrobial activity against bacteria, yeasts, fungi, and the like. Especially, it is useful for prevention and treatment of microbial infection caused by microorganisms which is resistive to wide variety of antibiotics. It is also useful for treatment of various matters such as drugs, foods, and the like with safety and great efficiency.

We claim:

1. An antimicrobial agent consisting essentially of (A) one or more of substantially purified and isolated antimicrobial peptides consisting of an amino acid sequence selected from the group consisting of SEQ ID Nos. 10–30 and 32 and (B) one or more compounds selected from the group consisting of tocopherol, cyclodextrin, glycerin-fatty acid ester, alcohol, chitosan, cysteine, and cholic acid, wherein component (B) is present in amounts sufficient to increase the antimicrobial effects of the antimicrobial peptide (A).

2. An antimicrobial agent consisting essentially of (A) one or more of substantially purified and isolated antimicrobial peptides consisting of an amino acid sequence selected from the group consisting of SEQ ID Nos. 1–32 and (C) at least an antibiotic selected from the group consisting of tetracycline antibiotics, penicillin, and antituberculosis drugs, wherein component (C) is present in amounts sufficient to increase the antimicrobial effects of the antimicrobial peptide (A).

3. An antimicrobial agent consisting essentially of (A) one or more of substantially purified and isolated antimicrobial peptides consisting of an amino acid sequence selected from the group consisting of SEQ ID Nos. 10–30 and 32 and (B) one or more compounds selected from the group consisting of tocopherol, cyclodextrin, glycerin-fatty acid ester, alcohol, chitosan, cysteine, and cholic acid and (C) at least an antibiotic selected from the group consisting of tetracycline antibiotics, penicillin, and antituberculosis drugs, wherein components (B) and (C) are present in amounts sufficient to increase the antimicrobial effects of the antimicrobial peptide (A).

4. A method for treatment of a matter with at antimicrobial agent consisting essentially of (A) one or more of substantially purified and isolated antimicrobial peptides consisting of an amino acid sequence selected from the group consisting of SEQ ID Nos. 10–30 and 32 and (B) one or more compounds selected from the group consisting of tocopherol, cyclodextrin, glycerin-fatty acid ester, alcohol, chitosan, cysteine, and cholic acid, wherein component (B) is present in amounts sufficient to increase the antimicrobial effects of the antimicrobial peptide (A).

5. A method for treatment of a matter with an antimicrobial agent consisting essentially of (A) one or more of substantially purified and isolated antimicrobial peptides consisting of an amino acid sequence selected from the group consisting of SEQ ID Nos. 10–30 and 32 and (C) at least one antibiotic selected from the group consisting of tetracycline antibiotics, penicillin, and antituberculosis drugs.

6. A method of treatment of a matter with an antimicrobial agent consisting essentially of (A) one or more of substantially purified and isolated antimicrobial peptides consisting of an amino acid sequence selected from the group consisting of SEQ ID Nos. 10–30 and 32 and (B) one or more compounds selected from the group consisting of tocopherol, cyclodextrin, glycerin-fatty acid ester, alcohol, chitosan, cysteine, and cholic acid, and (C) at least one antibiotic selected from the group consisting of tetracycline antibiotics, penicillin, and antituberculosis drugs wherein components (B) and (C) are present in amounts sufficient to increase the antimicrobial effects of the antimicrobial peptide (A).

\* \* \* \* \*

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="Xaa is an amino acid other
            than Cys"

( x i ) SEQUENCE DESCRIPTION: SEQ ID NO:1:

```
Lys  Xaa  Xaa  Xaa  Xaa  Gln  Xaa  Xaa  Met  Lys  Lys
 1                    5                         1 0
```

( 2 ) INFORMATION FOR SEQ ID NO:2:

( i ) SEQUENCE CHARACTERISTICS:
        ( A ) LENGTH: 11 amino acids (B) TYPE: amino acid
(C) STRANDEDNESS: single
(D) TOPOLOGY: linear (ii) MOLECULE TYPE: peptide (ix) FEATURE:
(A) NAME/KEY:
(B) LOCATION:
(C) IDENTIFICATION METHOD:
(D) OTHER INFORMATION: /note="Xaa is an amino acid other than Cys"

(xi) SEQUENCE DESCRIPTION: SEQ ID NO:2:

```
Lys Xaa Xaa Xaa Xaa Gln Xaa Xaa Met Arg Lys
 1               5                    10
```

(2) INFORMATION FOR SEQ ID NO:3:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY:
(B) LOCATION:
(C) IDENTIFICATION METHOD:
(D) OTHER INFORMATION: /note="Xaa is an amino acid other than Cys"

(xi) SEQUENCE DESCRIPTION: SEQ ID NO:3:

```
Arg Xaa Xaa Xaa Xaa Arg
 1               5
```

(2) INFORMATION FOR SEQ ID NO:4:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY:
(B) LOCATION:
(C) IDENTIFICATION METHOD:
(D) OTHER INFORMATION: /note="Xaa is an amino acid other than Cys"

(xi) SEQUENCE DESCRIPTION: SEQ ID NO:4:

```
Lys Xaa Xaa Xaa Xaa Arg
 1               5
```

(2) INFORMATION FOR SEQ ID NO:5:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY:
(B) LOCATION:
(C) IDENTIFICATION METHOD:
(D) OTHER INFORMATION: /note="Xaa is an amino acid other than Cys"

( x i ) SEQUENCE DESCRIPTION: SEQ ID NO:5:

Lys Xaa Xaa Xaa Xaa Lys
1               5

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="Xaa is an amino acid other
        than Cys"

( x i ) SEQUENCE DESCRIPTION: SEQ ID NO:6:

Arg Xaa Xaa Xaa Xaa Lys
1               5

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="Xaa is an amino acid other
        than Cys"

( x i ) SEQUENCE DESCRIPTION: SEQ ID NO:7:

Arg Xaa Xaa Xaa Arg
1             5

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="Xaa is an amino acid other
        than Cys"

( x i ) SEQUENCE DESCRIPTION: SEQ ID NO:8:

Lys Xaa Xaa Xaa Arg
1             5

( 2 ) INFORMATION FOR SEQ ID NO:9:

( i ) SEQUENCE CHARACTERISTICS:

(A) LENGTH: 5 amino acids
(B) TYPE: amino acid
(C) STRANDEDNESS: single
(D) TOPOLOGY: linear (ii) MOLECULE TYPE: peptide (ix) FEATURE:
(A) NAME/KEY:
(B) LOCATION:
(C) IDENTIFICATION METHOD:
(D) OTHER INFORMATION: /note="Xaa is an amino acid other than Cys"

(xi) SEQUENCE DESCRIPTION: SEQ ID NO:9:

Arg Xaa Xaa Xaa Lys
 1               5

(2) INFORMATION FOR SEQ ID NO:10:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:10:

Phe Gln Trp Gln Arg Asn
 1               5

(2) INFORMATION FOR SEQ ID NO:11:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:11:

Phe Gln Trp Gln Arg
 1               5

(2) INFORMATION FOR SEQ ID NO:12:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:12:

Gln Trp Gln Arg
 1

(2) INFORMATION FOR SEQ ID NO:13:

(i) SEQUENCE CHARACTERISTICS:
(A) LENGTH: 3 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:13:

Trp Gln Arg
1

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Arg Arg Trp Gln Trp
1                   5

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

Arg Arg Trp Gln
1

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

Trp Gln Trp Arg
1

( 2 ) INFORMATION FOR SEQ ID NO:17:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

Gln Trp Arg
1

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
Leu Arg Trp Gln Asn Asp
1               5
```

( 2 ) INFORMATION FOR SEQ ID NO:19:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:19:

```
Leu Arg Trp Gln Asn
1               5
```

( 2 ) INFORMATION FOR SEQ ID NO:20:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:20:

```
Leu Arg Trp Gln
1
```

( 2 ) INFORMATION FOR SEQ ID NO:21:

( i ) SEQUENCE CHARACTERISTICS:
    ( A ) LENGTH: 3 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:21:

```
Arg Trp Gln
1
```

( 2 ) INFORMATION FOR SEQ ID NO:22:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY:
    ( B ) LOCATION:
    ( C ) IDENTIFICATION METHOD:
    ( D ) OTHER INFORMATION: /note="Cys residues are linked by
      disulfide bond"

( x i ) SEQUENCE DESCRIPTION: SEQ ID NO:22:

```
Lys Cys Arg Arg Trp Gln Trp Arg Met Lys Lys Leu Gly Ala Pro
1               5                   10                  15
Ser Ile Thr Cys Val
                20
```

( 2 ) INFORMATION FOR SEQ ID NO:23:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY:
    ( B ) LOCATION:
    ( C ) IDENTIFICATION METHOD:
    ( D ) OTHER INFORMATION: /note="Cys residues are protected
        to prevent disulfide bond formation"

( x i ) SEQUENCE DESCRIPTION: SEQ ID NO:23:

```
Lys Cys Arg Arg Trp Gln Trp Arg Met Lys Lys Leu Gly Ala Pro
  1               5                  10                  15
Ser Ile Thr Cys Val
                 20
```

( 2 ) INFORMATION FOR SEQ ID NO:24:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="Cys residues are linked by
            disulfide bond"

( x i ) SEQUENCE DESCRIPTION: SEQ ID NO:24:

```
Lys Cys Phe Gln Trp Gln Arg Asn Met Arg Lys Val Arg Gly Pro
                  5                  10                  15
Pro Val Ser Cys Ile
                 20
```

( 2 ) INFORMATION FOR SEQ ID NO:25:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="Cys residues are protected
            to prevent disulfide bond"

( x i ) SEQUENCE DESCRIPTION: SEQ ID NO:25:

```
Lys Cys Phe Gln Trp Gln Arg Asn Met Arg Lys Val Arg Gly Pro
  1               5                  10                  15
Pro Val Ser Cys Ile
                 20
```

( 2 ) INFORMATION FOR SEQ ID NO:26:

( i ) SEQUENCE CHARACTERISTICS:
        ( A ) LENGTH: 25 amino acids (B) TYPE: amino acid
(C) STRANDEDNESS: single
(D) TOPOLOGY: linear (ii) MOLECULE TYPE: peptide (ix) FEATURE:
(A) NAME/KEY:
(B) LOCATION:
(C) IDENTIFICATION METHOD:
(D) OTHER INFORMATION: /note="Cys residues are linked by disulfide bond"

(xi) SEQUENCE DESCRIPTION: SEQ ID NO:26:

```
Phe Lys Cys Arg Arg Trp Gln Trp Arg Met Lys Lys Leu Gly Ala
1               5                   10                  15
Pro Ser Ile Thr Cys Val Arg Arg Ala Phe
                20                  20
```

(2) INFORMATION FOR SEQ ID NO:27:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:27:

```
Lys Thr Arg Arg Trp Gln Trp Arg Met Lys Lys
1               5                   10
```

(2) INFORMATION FOR SEQ ID NO:28:

(i) SEQUENCE CHARACTERISTICS:
(A) LENGTH: 38 amino acids
(B) TYPE: amino acid
(C) STRANDEDNESS: single
(D) TOPOLOGY: linear (ii) MOLECULE TYPE: peptide (ix) FEATURE:
(A) NAME/KEY:
(B) LOCATION:
(C) IDENTIFICATION METHOD:
(D) OTHER INFORMATION: /note="Cys residues at positions 16 and 33 are linked by disulfide bond"

(xi) SEQUENCE DESCRIPTION: SEQ ID NO:28:

```
Lys Asn Val Arg Trp Cys Thr Ile Ser Gln Pro Glu Trp Phe Lys
1               5                   10                  15
Cys Arg Arg Trp Gln Trp Arg Met Lys Lys Leu Gly Ala Pro Ser
                20                  25                  30
Ile Thr Cys Val Arg Arg Ala Phe
                35
```

(2) INFORMATION FOR SEQ ID NO:29:

(i) SEQUENCE CHARACTERISTICS:
(A) LENGTH: 32 amino acids
(B) TYPE: amino acid
(C) STRANDEDNESS: single
(D) TOPOLOGY: linear (ii) MOLECULE TYPE: peptide (ix) FEATURE:
(A) NAME/KEY:
(B) LOCATION:

( C ) IDENTIFICATION METHOD:
( D ) OTHER INFORMATION: /note="Cys residues are linked by disulfide bond"

( x i ) SEQUENCE DESCRIPTION: SEQ ID NO:29:

Thr Ile Ser Gln Pro Glu Trp Phe Lys Cys Arg Arg Trp Gln Trp
1               5                   10                  15

Arg Met Lys Lys Leu Gly Ala Pro Ser Ile Thr Cys Val Arg Arg
                20                  25                  30

Ala Phe ( 2 ) INFORMATION FOR SEQ ID NO:30:

( i ) SEQUENCE CHARACTERISTICS:
( A ) LENGTH: 36 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY:
( B ) LOCATION:
( C ) IDENTIFICATION METHOD:
( D ) OTHER INFORMATION: /note="Cys residues at positions 9 and 26 are linked by disulfide bond, and Cys residue at position 35 is linked by disulfide bond to Cys residue at position 10 of SEQ ID No. 32"

( x i ) SEQUENCE DESCRIPTION: SEQ ID NO:30:

Val Ser Gln Pro Glu Ala Thr Lys Cys Phe Gln Trp Gln Arg Asn
1               5                   10                  15

Met Arg Lys Val Arg Gly Pro Pro Val Ser Cys Ile Lys Arg Asp
                20                  25                  30

Ser Pro Ile Gln Cys Ile
                35

( 2 ) INFORMATION FOR SEQ ID NO:31:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY:
( B ) LOCATION:
( C ) IDENTIFICATION METHOD:
( D ) OTHER INFORMATION: /note="Xaa is an amino acid other than Cys"

( x i ) SEQUENCE DESCRIPTION: SEQ ID NO:31:

Lys Xaa Xaa Xaa Lys
1               5

( 2 ) INFORMATION FOR SEQ ID NO:32:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( i x ) FEATURE:

```
    ( A ) NAME/KEY:
    ( B ) LOCATION:
    ( C ) IDENTIFICATION METHOD:
    ( D ) OTHER INFORMATION: /note="Cys at position 10 is linked
            to Cys at position 35 of SEQ ID No. 10 by disulfide bond"

( x i ) SEQUENCE DESCRIPTION: SEQ ID NO:32:

Gly  Arg  Arg  Arg  Arg  Ser  Val  Gln  Trp  Cys  Ala
 1                  5                       1 0
```